United States Patent [19]
Dietz et al.

[11] Patent Number: 5,486,180
[45] Date of Patent: *Jan. 23, 1996

[54] APPARATUS FOR MILLING BONE

[75] Inventors: Terry L. Dietz, Columbia City; Richard D. Vanlaningham, Milford, both of Ind.

[73] Assignee: Zimmer, Inc., Warsaw, Ind.

[*] Notice: The term of this patent shall not extend beyond the expiration date of Pat. No. 5,344,423.

[21] Appl. No.: 258,114

[22] Filed: Jun. 10, 1994

Related U.S. Application Data

[63] Continuation-in-part of Ser. No. 832,098, Feb. 6, 1992, Pat. No. 5,344,423.

[51] Int. Cl.⁶ .................................................... A61F 5/04
[52] U.S. Cl. ................................................. 606/87; 606/86
[58] Field of Search ................................. 606/79, 82, 86, 606/87, 88, 89, 96, 97, 98, 179, 180; 623/20, 16

[56] References Cited

U.S. PATENT DOCUMENTS

| | | |
|---|---|---|
| 4,467,801 | 8/1984 | Whiteside . |
| 4,474,177 | 10/1984 | Whiteside . |
| 4,721,104 | 1/1988 | Kaufman et al. . |
| 4,952,214 | 8/1990 | Comparetto ............... 606/82 |
| 5,002,545 | 3/1991 | Whiteside ................. 606/80 |
| 5,035,699 | 7/1991 | Coates ...................... 606/86 |
| 5,047,032 | 9/1991 | Jellicoe .................... 606/83 |
| 5,098,436 | 3/1992 | Ferrante et al. ........... 606/88 |
| 5,100,409 | 3/1992 | Coates et al. ............. 606/87 |
| 5,176,684 | 1/1993 | Ferrante ................... 606/86 |
| 5,250,050 | 10/1993 | Poggie ..................... 606/79 |
| 5,344,423 | 9/1994 | Dietz ....................... 606/86 |
| 5,356,414 | 10/1994 | Cohen ..................... 606/86 |
| 5,417,695 | 5/1995 | Axelson, Jr. .............. 606/89 |

FOREIGN PATENT DOCUMENTS

| | | | |
|---|---|---|---|
| 0337901A1 | 10/1989 | European Pat. Off. | ........ A61B 17/14 |
| 415837 | 8/1990 | France | ........... 606/87 |
| WO88/04912 | 7/1988 | WIPO | ........... A61B 17/14 |

*Primary Examiner*—Robert A. Hafer
*Assistant Examiner*—David J. Kenealy
*Attorney, Agent, or Firm*—Cary R. Reeves

[57] ABSTRACT

An apparatus is provided for milling bone. The apparatus includes a template having a reference surface for controlling depth of cut and a track for guiding the cutter in two dimensions to cut a planar surface.

7 Claims, 2 Drawing Sheets

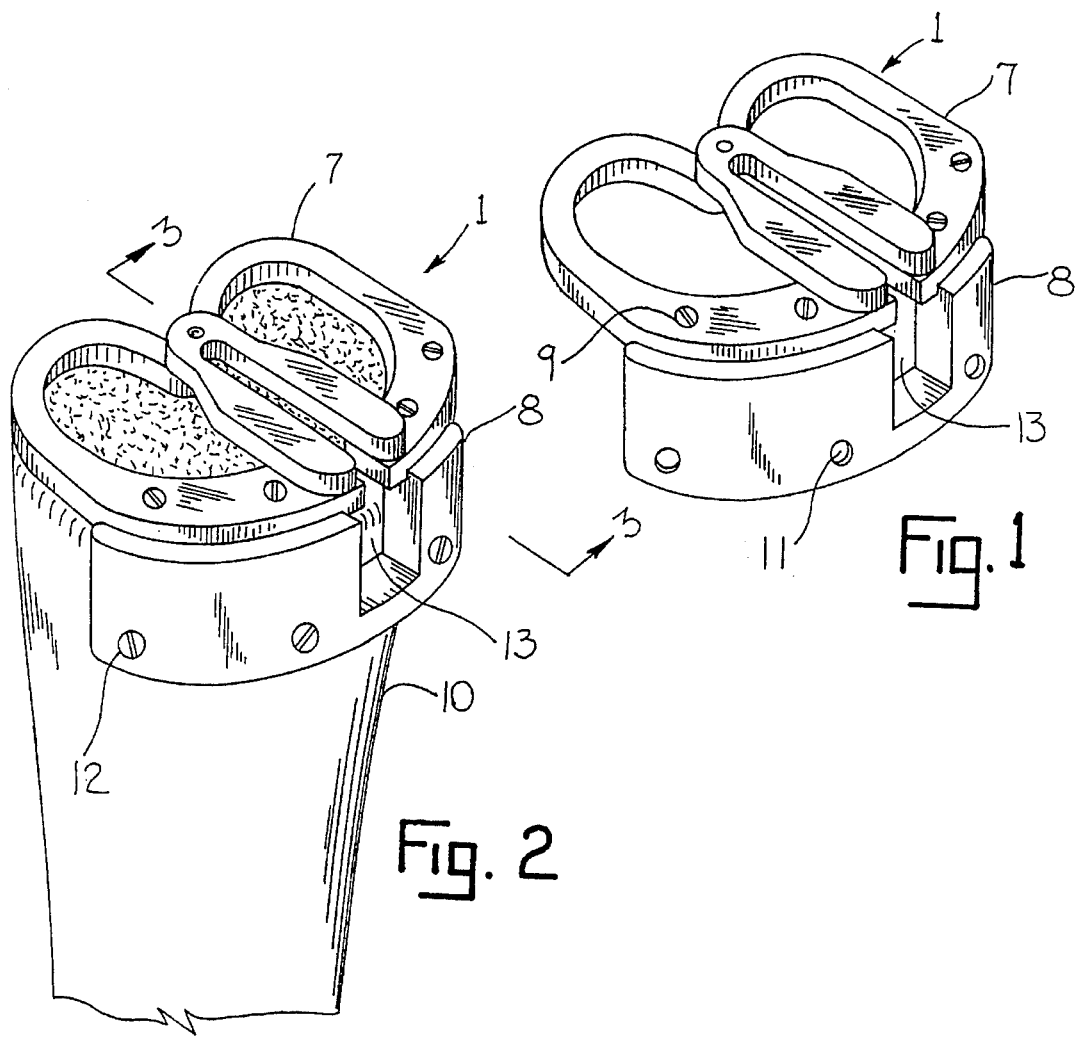
Fig. 1
Fig. 2
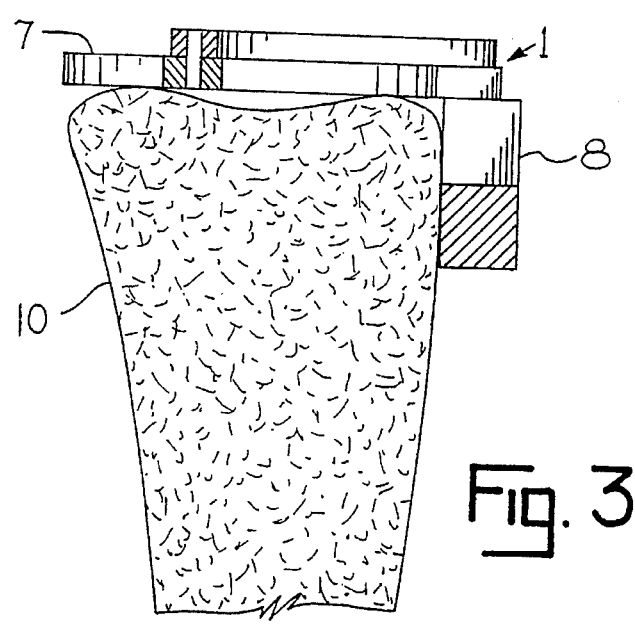
Fig. 3

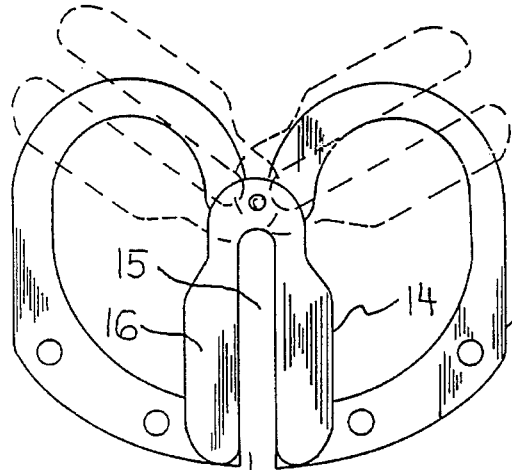
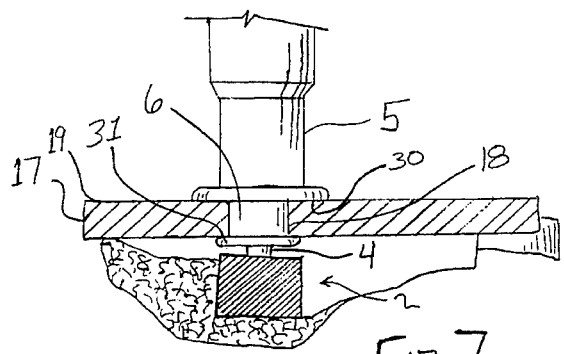
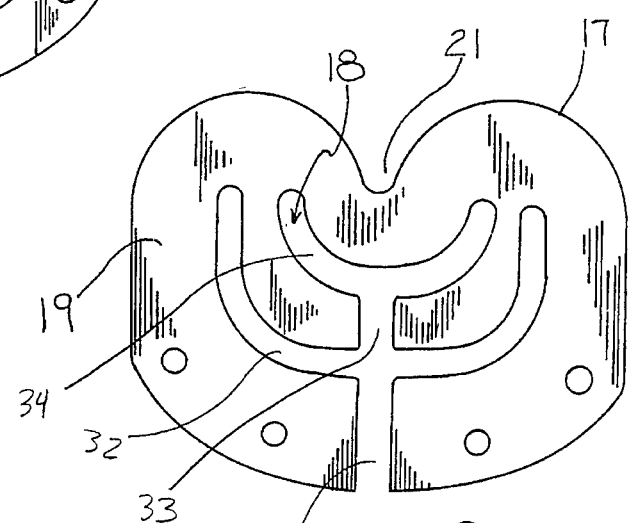
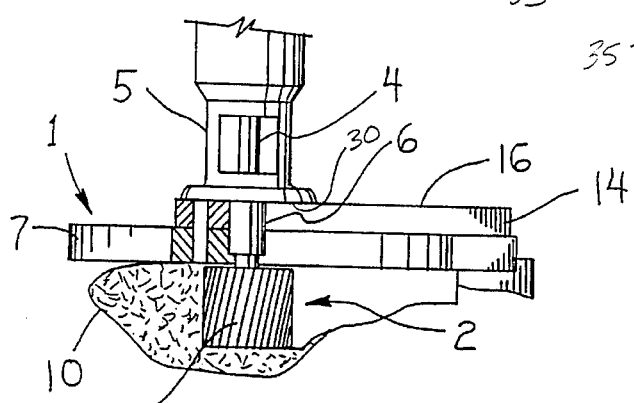

APPARATUS FOR MILLING BONE

CROSS-REFERENCE TO RELATED APPLICATION

This application is a continuation-in-part of application Ser. No. 07/832,098, filed Feb. 6, 1992 now U.S. Pat. No. 5,344,423.

FIELD OF THE INVENTION

This invention relates to an apparatus for cutting bone and has specific relevance to an apparatus for milling a planar surface on a portion of a bone.

BACKGROUND OF THE INVENTION

Surgical procedures for removing a defective joint and replacing it with a prosthetic joint are well known. To accommodate the prosthetic joint it is very often necessary to remove a portion of the bone.

Heretofore, a generally flat surgical saw blade was used to cut the bone to remove the required portion of the bone. The saw blade could be either hand operated or powered in a reciprocating or oscillating motion. Typically, a guide would be connected adjacent the bone to guide the blade along the bone to assist in making a more precise cut. Typical saw blades are elongated and may bend slightly during cutting which can add to the inaccuracy of the cut or form small variations in the resulting surface requiring additional surface preparation before the prosthesis is attached.

SUMMARY OF THE INVENTION

The milling apparatus of this invention includes a guide connected to the exposed end portion of the bone by a plurality of screws or other fastening device. The guide includes a template having a reference surface which determines the milling depth. The guide also includes a track defined by the template to accommodate the shaft of a milling device. In use, a milling device is positioned such that the cutting teeth of the milling device are engageable with the bone stock to be removed. A shaft of the milling device extends through the track and is connectable to a rotary power source. While the power source drives it, the milling device is manually moved within the template as guided by the track of the template to mill the bone to a flat planar surface. Once the bone is milled, the guide is removed.

Accordingly, it is an object of the invention to provide a milling guide for a bone.

Another object of the invention is to provide a bone milling guide having a track to accommodate a mill cutter.

Further objects of the invention will become apparent upon a reading of the following description taken with the accompanying drawings.

BRIEF DESCRIPTION OF THE DRAWINGS

FIG. 1 is a perspective view of the invention.

FIG. 2 is a perspective view of the invention connected to a tibia to be milled.

FIG. 3 is a sectional view taken along line 3—3 of FIG. 1.

FIG. 4 is a plan view of the guide of FIGS. 1–3.

FIG. 5 is a sectional view of the proximal tibia being milled with a mill guided by the guide of the invention.

FIG. 6 is a plan view of a preferred embodiment of the guide of the invention.

FIG. 7 is a sectional view of the proximal tibia being milled with a mill guided by the preferred embodiment of the guide of the invention.

DESCRIPTION OF THE PREFERRED EMBODIMENTS

The preferred embodiments herein described are not intended to be exhaustive or to limit the invention to the precise forms disclosed. Rather, they are chosen and described to best explain the invention so that others skilled in the art might utilize their teachings.

Referring now to FIGS. 1–5 an exemplary apparatus for producing a planar surface on a portion of a tibia is illustrated and includes a guide 1 and a bone milling device. The bone milling device of FIG. 5 includes a burr 2 with a cutting portion 3 for milling bone and a shaft portion 4 connecting the cutting portion to a driving means. Preferably the cutting portion has cutting teeth on its distal end as well as along its sides. It may take the form of industrial end mills, router bits, or other suitable shape. While the shaft may engage the guide directly, it is preferable for the milling device to provide a guide engaging portion or nose 5 with a nose surface 30 and an extending cannulated nipple 6. The shaft 4 extends through the nipple 6. The guide includes a template 7 and a base 8. The template is connected to the base by a plurality of screws 9 or some other fastening means. Even more preferably the template and base are integrated into a single piece. The base is slightly arcuate to conform to the outer contour of a patient's tibia 10 just below the knee joint. Transverse through bores 11 are formed in the base for accommodating bone screws 12 to connect the milling guide to the tibia. The base and template further have burr openings 13 and 20 to allow the burr to pass. The template is generally planar and includes a peripheral rim shaped as illustrated in the figures. In the embodiment of FIGS. 1–5, the template defines an open interior defining the limits of travel of the burr. It further comprises a pivot arm 14 which contains a slot or track 15 to accommodate the nipple 6 of the milling device. The top of the pivot arm forms a reference surface 16 engageable with the nose surface 30 of the milling device, to control depth of cut.

In use, the guide is positioned at the desired height above the tibial articular surface by any method know in the art and securely fastened with bone screws through the base. The burr 2, connected to the power source, is placed in the burr openings 13 and 20 and the nose and nipple are placed adjacent the reference surface and track. With the burr being driven to cut bone, the pivot arm 14 is pivoted and the nipple 6 is moved along the track 15 to guide the burr so that it moves in two dimensions over the tibia to create a planar surface substantially parallel to the reference surface. After the tibia has been milled the guide is removed and a tibial plate prosthesis may be implanted.

Another, more preferred, template embodiment is depicted in FIGS. 6 and 7. The substantially planar template 17 contains a fixed track 18 for guiding the burr and a reference surface 19 to control depth of cut. The track is shaped so that a portion of the path that the burr cuts overlaps other portions of the path to yield a continuous planar cut surface. Burrs having different diameters might require different track shapes to achieve this result. Preferably the track 18, comprises a non-linear track such as a plurality of branching slots 32, 33 and 34. In the embodiment shown in FIG. 6, the track 18 comprises arcuate slots 32 and 34 joined by straight slot 33. The track 18 could also comprise linear slots branching in different directions or the track 18 could have a serpentine shape. In all of these embodiments however, following the track in its entirety requires motion in more than one direction. The nose 5 preferably has a retainer 31 formed at the end of the nipple 6. The retainer 31 has a larger diameter than the width of the slots comprising the track 18 so that the burr 2 cannot be withdrawn vertically from the track 18. The nipple 6 fits closely in the track 18, the nipple 6 diameter being approximately equal to the width of the slots comprising the track 18. The close fit of the nipple 6 in the track 18 constrains the nipple 6 and thus the burr 2 to motion along the track 18 corresponding to the shape of the track. In other words, as the nipple 6 and burr 2 are guided along the track 18 they are forced to follow a non-linear path. The burr 2 also has a diameter larger than the width of the slots comprising the branched track 18.

In use, the preferred guide of FIGS. 6 and 7 is positioned above the tibial articular surface at the desired height. The nipple 6 is placed in opening 35. Nose surface 30 rests on the reference surface 19 of the template 17 and retainer 31 is adjacent the lower surface of the template 17. With the burr 2 being driven to cut bone, the nipple 6 is guided along the track 18 causing the burr 2 to cut paths in the bone corresponding to the non-linear shape of the track 18. However, the burr 2 diameter is such that the paths cut into the bone overlap and the burr 2 creates a planar surface on the bone substantially parallel to the top of the upper surface of the template 17. While the burr 2 may be guided to cut an area that is within the periphery of the template 17 or an area that extends beyond the template 17, it is preferable that the periphery of the template 17 be made to correspond to the outer limits of the paths cut by the burr 2 to allow an operator to determine precisely which tissues will be cut. It is also preferable to provide a variety of guides to accommodate a variety of bone sizes and shapes and variously shaped cut areas. For example, the exemplary guide shown provides an uncut posterior region 21 as would be suitable for a posterior cruciate ligament retaining tibial prosthesis.

While the preceding exemplary embodiments have focused on milling the tibial articular surface for a total knee joint prosthesis, it will be understood that the techniques described are applicable to unicondylar knee replacements as well as other joints and other bone surfaces, the guide geometry being adjusted accordingly. Likewise, it will be understood by those skilled in the art that numerous modifications to and departures from the embodiments hereinabove can be made without departing from the spirit and scope of the invention defined by the appended claims.

We claim:

1. An apparatus for producing a planar surface on a portion of a bone, the apparatus comprising a milling device, a guide, and means for attaching the guide to the bone, the guide having a reference surface and a non-linear track, the reference surface being adapted to engage the milling device to constrain the milling device to motion in a plane, the non-linear track having a width approximately equal to the width of a portion of the milling device, said portion engageable within the track, the close fit of said portion within the track forcing the milling device to move in a non-linear motion along the non-linear track such that when the milling device is guided along the track, the milling device will form the planar surface on the bone parallel to the reference surface.

2. The apparatus of claim 1 wherein the track comprises branching slots, the milling device cutting a path as it is guided along the track, a first portion of the path the milling device cuts corresponding to one of the branching slots and a second portion of the path the milling device cuts corresponding to another of the branching slots, the slots being positioned such that the first portion of the path overlaps the second portion of the path to yield a continuous planar cut surface.

3. The apparatus of claim 1 wherein the track comprises a serpentine slot, the slot being shaped such that as the milling device is guided along the track it cuts a path, a portion of the path the milling device cuts overlapping other portions of the path to yield a continuous planar cut surface.

4. The apparatus of claim 1 wherein the portion includes a nose attached to the milling device and in engagement with the guide, the nose comprising:

a nose surface slidably engaging the reference surface, a nipple extending beyond the nose surface, the nipple fitting closely within the track, and a retainer formed at the end of the nipple, the retainer engaging a lower surface of the guide thus preventing the nipple from being withdrawn vertically from the track.

5. The apparatus of claim 4 wherein the retainer is circular and has a diameter, the diameter of the retainer being greater than the width of the track.

6. An apparatus for producing a planar surface on a portion of a bone, the apparatus comprising:

a milling device, the milling device including a cutting portion having a diameter; and a guide, the guide including:

means for attaching the guide to the bone;

a reference surface adapted to engage the milling device to constrain the milling device to motion in a plane; and a non-linear track for engaging the milling device and constraining the milling device to non-linear motion, the track having a width, the diameter of the cutting portion being greater than the width of the track such that when the milling device is guided along the non-linear track, the milling device forms the planar surface on the bone parallel to the reference surface.

7. The apparatus of claim 6 wherein the non-linear track comprises branching slots.

* * * * *